United States Patent [19]

Kobayashi et al.

[11] 4,434,306
[45] Feb. 28, 1984

[54] PERFUME COMPOSITION

[75] Inventors: Toyohiko Kobayashi; Haruki Tsuruta, both of Kanagawa, Japan

[73] Assignee: Takasago Perfumery Co., Ltd., Tokyo, Japan

[21] Appl. No.: 330,358

[22] Filed: Dec. 14, 1981

[30] Foreign Application Priority Data

Dec. 17, 1980 [JP] Japan ................................. 55-178308

[51] Int. Cl.³ ..................... C07C 35/22; C07C 35/24; C07C 35/26; C07C 35/28
[52] U.S. Cl. ................................. 568/820; 252/522 R; 568/819
[58] Field of Search .................... 252/522 R; 568/820, 568/819

[56] References Cited

U.S. PATENT DOCUMENTS 3,929,676  12/1975  Chappell et al. ............... 252/522 R
4,163,737   8/1979  Sanders et al. ................. 252/522 R
4,218,348   8/1980  Mulder et al. .................. 252/522 R Primary Examiner—Helen M. S. Sneed
Attorney, Agent, or Firm—Sughrue, Mion, Zinn, Macpeak and Seas

[57] ABSTRACT

A perfume composition is described, which contains at least one compound of bicyclo[2,2,2]octane and bicyclo[2,2,2]octene derivatives represented by the general formula (I)

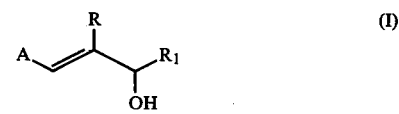

wherein the symbols are the same as defined hereinbefore.

5 Claims, No Drawings

PERFUME COMPOSITION

FIELD OF THE INVENTION

The present invention relates to novel perfume compositions, and more particularly, to perfume compositions containing at least one compound of bicyclo[2,2,-2]octane and bicyclo[2,2,2]octene derivatives.

BACKGROUND OF THE INVENTION

In general, Indian sandalwood oil is widely used as an important perfume component in the perfume industry. Recently, however, the price of natural sandalwood oil has risen because of a shortage of raw material thereof, and access to natural sandalwood oil has become increasingly difficult. Various investigations have therefore been made to produce a substitute for sandalwood oil.

SUMMARY OF THE INVENTION

As a result of extensive studies on pyronene and derivatives thereof resulting from thermal isomerization of alloocimene, which is easily obtained from pinene collected from pinaceous plants, it has been found that bicyclo[2,2,2]octane and bicyclo[2,2,2]octene derivatives represented by formula (I) below have excellent properties as perfume components, i.e., are sandalwood oil-like odor with high tenacity and naturality.

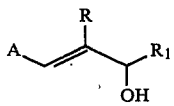
(I)

wherein R is a hydrogen atom or a methyl group, $R_1$ is a hydrogen atom, a methyl group, or an ethyl group, and A is

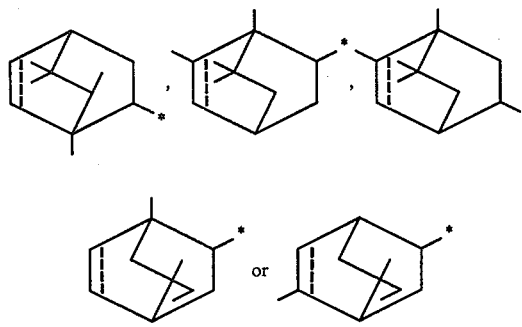

wherein the dotted line indicates the position of either a double bond or a single bond, and the asterisk * indicates the position of bonding to the remaining portion of formula (I).

The present invention, therefore, provides a perfume composition containing at least one compound of bicyclo[2,2,2]octane and bicyclo[2,2,2]octene derivatives represented by formula (I)

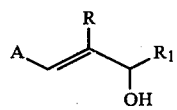
(I)

wherein R, $R_1$ and A are the same as defined above.

DETAILED DESCRIPTION OF THE INVENTION

It has heretofore been known that when alloocimene (1) is isomerized by heating at about 500° C., a mixture (1:2:1) of α-pyronene (2), β-pyronene (3), and 1,3-dimethyl-1-ethyl-cyclohexadiene (4) is obtained in a combined yield of about 70%, as illustrated in the reaction equation shown below (see Y. Matsubara, et al., *Yuki Gosei Kagaku*, 31, 928 (1973), and C. Wesley et al., *International Congress Essential Oils*, (Pap.), 6th, 1974, 140 (*Chem. Abstracts*, Vol. 84, 135828f (1976)).

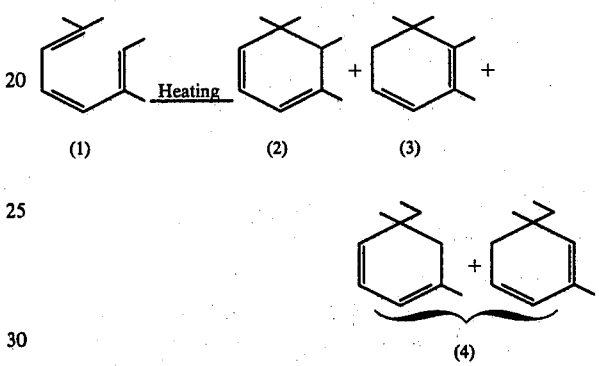

The mixture is separated into (2), (3) and (4). When each of (2), (3) and (4) is reacted with acrolein (5) by the Diels Alder reaction, there is obtained a so-called Diels-Alder adduct, i.e., a bicyclo[2,2,2]oct-5-ene derivative having a formyl group. More particularly, it is known that as illustrated in the reaction equation shown below, (6) is obtained from α-pyronene (2), (7) is obtained from β-pyronene (3), and (8) is obtained from 1,3-dimethyl-1-ethyl-cyclohexadiene (4), and therefore, a mixture of (6), (7), and (8) is obtained from a mixture of (2), (3) and (4) (see Y. Matsubara et al., *Kindai Riko Kenkyo Hokoku*, 10, 53 (1975) (*Chem. Abstracts*, Vol. 84, 3129592 (1976)), ibid., Vol. 10, 61 (1975) (*Chem. Abstracts*, Vol. 84, 31260y (1976)), and Japanese Patent Application (OPI) No. 20160/74 (the term "OPI" as used herein refers to a "published unexamined Japanese patent application")).

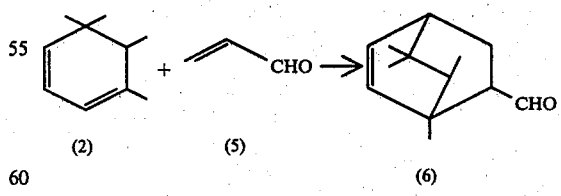

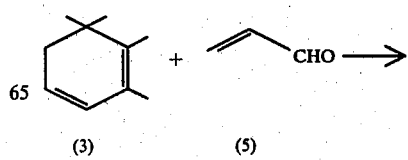

-continued

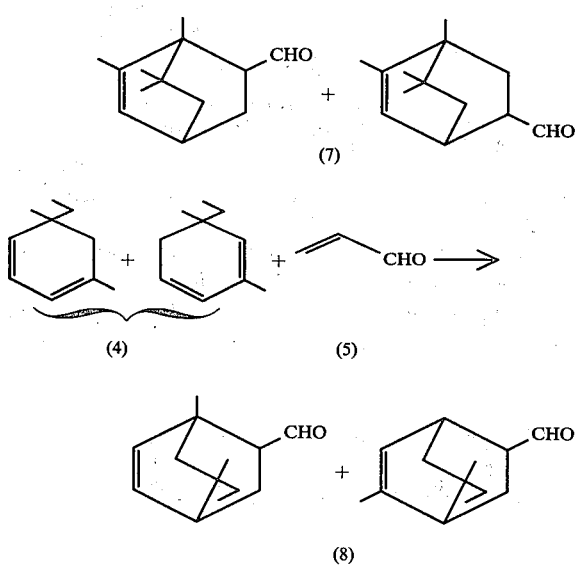

The compounds represented by formula (I), which are an essential component of the perfume composition of the invention, are prepared as follows:

(1) Compounds (6), (7) and (8) are condensed with aldehydes or ketones in the presence of an alkali to form Aldol condensates. These Aldol condensates are reduced with sodium boron hydride or the like to obtain bicyclo[2,2,2]octene derivatives (corresponding to compounds of formula (I) wherein the double bond indicated by the dotted line is present).

(2) Compounds (6), (7) and (8) are subjected to catalytic reduction in the presence of a catalyst, e.g., palladium-activated carbon, to saturate the double bond thereof. The resulting compounds are treated in the same manner as in (1) above to obtain bicyclo[2,2,2]octane derivatives (corresponding to compounds of formula (I) wherein a single bond is present at the position of the dotted line).

Aldehydes as used herein include acetaldehyde and propionaldehyde. Ketones as used herein include acetone, methyl ethyl ketone, and diethyl ketone.

As an embodiment of a method of preparing the compound of formula (I), below there are shown reaction schemes for preparing 1-(1,7,8,8-tetramethyl-bicyclo[2,2,2]oct-5-ene-2-yl)-2-methyl-3-hydroxy-1-pentene (11) and 1-(1,7,8,8-tetramethyl-bicyclo[2,2,2]octane-2-yl)-2-methyl-3-hydroxy-1-pentene (14) from 1,7,8,8-tetramethyl-bicyclo[2,2,2]oct-5-ene-2-carboxyaldehyde (6), which is a Diels Alder adduct of α-pyronene (2) and acrolein, and diethyl ketone (9).

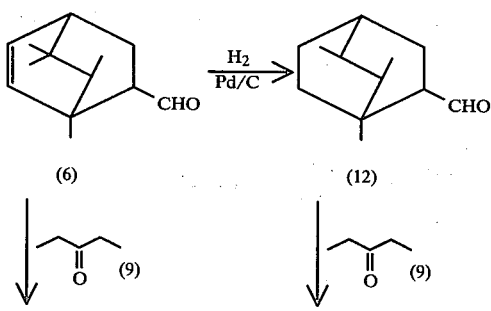

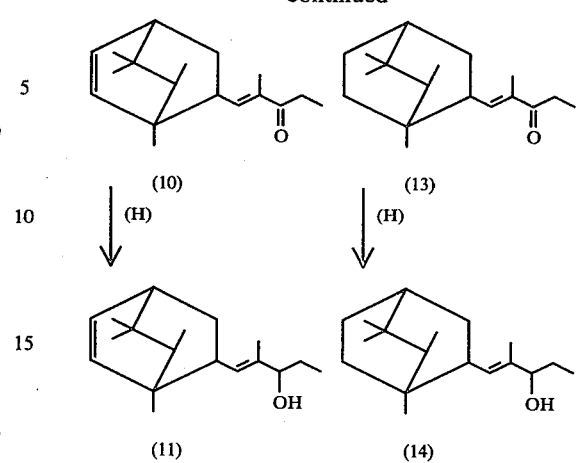

The compounds represented by formula (I) all have a musk-like or sandalwood-like odor which varies delicately depending on the particular compound. For practical use, therefore, the compounds can be used in the form of a mixture as a perfume component. For example, when a compound represented by the formula (I) is produced from alloocimene as a starting material, many intermediate compounds are formed as described hereinbefore. It is advantageous from an industrial viewpoint that such intermediate compounds can be used as is in the subsequent step. In other words, such intermediate compounds are valuable perfumes which can be used directly in the perfume industry without fractional distillation.

The perfume composition of the invention has a wide variety of applications; for example, it can be used in a perfume, ead de Cologne, hair care product, soap, a detergent, a room deodorant, a stick of incense, and the like.

The following synthesis examples and examples of the invention are provided to illustrate the invention in greater detail.

SYNTHESIS EXAMPLE 1

Alloocimene was isomerized by heating at 500° C., and the resulting mixture was separated and purified by distillation to obtain α-pyronene (2). The α-pyronene (2) and acrolein were subjected to a Diels-Alder reaction to form a Diels-Alder adduct (6). A mixture of 17 g of the Diels-Alder adduct (6), 100 g of diethyl ketone, 200 ml of methanol, and 10 g of 40% caustic soda was placed in a 500-ml reaction flask and reacted in reflux for 30 hours. The methanol and excessive diethyl ketone were distilled off under reduced pressure. The residue was poured into ice water and extracted with ethyl ether. The ethyl ether layer was separated and washed with water. The organic layer was dried using magnesium sulfate and the solvent was distilled off. When the residue was allowed to stand at room temperature, crystals were deposited. These crystals were filtered off and recrystallized from diisopropyl ether to thereby obtain 14.5 g of colorless crystals of 1-(1,7,8,8-tetramethyl-bicyclo[2,2,2]oct-5-ene-2-yl)-2-methyl-1-pentene-3-on (10). The melting point was 106° to 106.5° C. Instrumental analytical values for mass spectroscopy (MS), infrared (IR), and nuclear magnetic resonance (NMR) are shown below:

MS: M+ =260 m/e.

IR: 1660, 1635, 725 cm$^{-1}$.

NMR: 0.72 (3H, d, 7.0 Hz), 0.75 (3H, s), 0.94 (3H, s), 1.05 (3H, t, 7.0 Hz), 1.06 (3H, s), 1.74 (3H, bs), 2.0 to 2.5 (3H, m), 2.61 (2H, q, 7.0 Hz), 5.74 (1H, d, 9.0 Hz), 6.23 (1H, bd, 10.0 Hz), 6.40 (1H, dd, 9.0, 7.0 Hz).

MS was measured using "HITACHI M-80" (Hitachi Ltd.), IR was measured using "JASCO A-3" (Japan Spectroscopic Co., Ltd.), and NMR was measured using "JEOL FX-900" (Jeol Ltd.). Hereinafter the same instruments were used.

A mixture of 14.5 g of the ketone compound as prepared above, 30 ml of methanol, and 0.75 g of a 10% aqueous potassium hydroxide solution was placed in a 200-ml reaction flask. Then, at room temperature, a solution consisting of 0.05 g of caustic potash, 15 ml of water, 15 ml of methanol, and 1.5 g of sodium boron hydride was dropwise added thereto over a period of about one hour. The resulting mixture was reacted at room temperature for two hours, and subsequently at 55° C. for five hours, under stirring. The reaction solution was poured into ice water and extracted with ethyl ether. The ethyl ether layer was washed with water and dried with anhydrous Glauber's salt. Then the ethyl ether was distilled off. The residue was vacuum-distilled to obtain 13.2 g of a colorless liquid of 1-(1,7,8,8-tetramethyl-bicyclo[2,2,2]oct-5-ene-2-yl)-2-methyl-3-hydroxy-1-pentene (11) having a boiling point of 115° C. to 120° C. at 1 mmHg. The compound (11) had strong sandalwood-like odor. Instrumental analytical values are shown below:

MS: M+ =262 m/e.
IR: 3350, 725 cm$^{-1}$.
NMR: 0.65 to 1.10 (m), 1.56 (3H, bs), 1.96 (1H, m), 2.28 (2H, m), 3.83 (1H, t, 7.0 Hz), 4.96 (1H, bd, 9.0 Hz), 5.66 (1H, bd, 9.0 Hz), 6.30 (H, dd, 9.0, 7.0 Hz).

SYNTHESIS EXAMPLE 2

Using 9.2 g of a Diels-Alder adduct (7) of β-pyronene (3), which had been obtained by a conventional known method, and acrolein, 30 g of diethyl ketone, 50 ml of methanol, and 2 g of a 40% aqueous solution of caustic soda, 9.0 g of a ketone substance was prepared in the same manner as in Synthesis Example 1. Gas chromatographic analysis showed that the ketone compound was a mixture of 1-(1,6,7,7-tetramethyl-bicyclo[2,2,2]oct-5-ene-2-yl)-2-methyl-1-pentene-3-on and 1-(1,6,7,7-tetramethyl-bicyclo[2,2,2]oct-5-ene-3-yl)-2-methyl-1-pentene-3-on, and the ratio thereof was nearly 1:1. These compounds were isolated by gas chromatography under the conditions of 5% FFAP (free fatty acid polyester)/Uniport HP (carrier, a product of Gasukuro Kogyo Co., Ltd.), 5 mm×5 m, 230° C. The instrumental analytical values of the compounds are shown below:

1-(1,6,7,7-Tetramethyl-bicyclo[2,2,2]oct-5-ene-2-yl)-2-methyl-1-pentene-3-on

MS: M+ =260 m/e.
IR: 1670, 1635 cm$^{-1}$.
NMR: 0.76 (3H, s), 0.92 (3H, s), 1.04 (3H, s), 1.06 (3H, t, 7.0 Hz), 1.74 (6H, bs), 2.38 (1H, m), 2.62 (2H, q, 7.0 Hz), 2.92 (1H, td, 10.0, 4.0 Hz), 6.00 (1H, bd, 7 Hz).

1-(1,6,7,7-Tetramethyl-bicyclo[2,2,2]oct-5-ene-3-yl)-2-methyl-1-pentene-3-on

MS: M+ =260 m/e.
IR: 1670, 1635 cm$^{-1}$.

NMR: 0.76 (3H, s), 1.00 (3H, s), 1.02 (3H, s), 1.05 (3H, t, 7.0 Hz), 1.32 (2H, m), 1.76 (6H, bs), 2.04 (1H, dd, 12.5, 9 Hz), 2.63 (2H, q, 7.0 Hz), 5.83 (1H, bd, 7.0 Hz), 6.31 (1H, bd, 9.0 Hz).

Then 9 g of the ketone compound as prepared above was reduced with sodium boron hydride in the same manner as in Synthesis Example 1 to obtain 8.5 g of a colorless liquid having a boiling point of 117° to 125° C./1 mmHg. This colorless liquid had a strong sandalwood-like odor. Gas chromatographic analysis showed that the colorless liquid was a nearly 1:1 mixture of 1-(1-6,7,7-tetramethyl-bicyclo[2,2,2]oct-5-ene-2-yl)-2-methyl-3-hydroxy-1-pentene and 1-(1,6,7,7-tetramethyl-bicyclo[2,2,2]oct-5-ene-3-yl)-2-methyl-3-hydroxy-1-pentene. These compounds were isolated by gas chromatography under the same conditions as in Synthesis Example 2. The instrumental analytical values of the compounds are shown below:

1-(1,6,7,7-Tetramethyl-bicyclo[2,2,2]oct-5-ene-2-yl)-2-methyl-3-hydroxy-1-pentene MS: M+ =262 m/e.
IR: 3350 cm$^{-1}$.
NMR: 0.75 (3H, s), 0.82 (3H, t, 7.0 Hz), 0.94 (3H, s), 1.02 (3H, s), 1.58 (3H, bs), 1.70 (3H, bs), 2.28 (1H, m), 2.72 (1H, td, 10.0, 4.0 Hz), 3.83 (1H, t, 7.0 Hz), 4.98 (1H, bd, 11 Hz), 5.88 (1H, bd, 7.0 Hz).

1-(1,6,7,7-Tetramethyl-bicyclo[2,2,2]oct-5-ene-3-yl)-2-methyl-3-hydroxy-1-pentene MS: M+ =262 m/e.
IR: 3340 cm$^{-1}$.
NMR: 0.75 (3H, s), 0.81 (3H, t, 7.0 Hz), 0.98 (6H, s), 1.58 (3H, bs), 1.64 (3H, bs), 1.8 to 2.6 (3H, m), 3.81 (1H, t, 7.0 Hz), 5.08 (1H, bd, 9.0 Hz), 5.75 (1H, bd, 7.0 Hz).

SYNTHESIS EXAMPLE 3

Using 9.0 g of a Diels-Alder adduct (8) of 1,3-dimethyl-1-ethyl-cyclohexadiene (4), which had been prepared by a conventional known method, and acrolein, 30 g of diethyl ketone, 50 ml of methanol, and 2 g of a 40% aqueous solution of caustic soda, 8.4 g of the corresponding ketone was prepared in the same manner as in Synthesis Example 1. The instrumental analytical values of the substance were as follows:

MS: M+ =260 m/e.
IR: 1760, 1640, 720 cm$^{-1}$.

Then, 8.4 g of the ketone compound was reduced with sodium boron hydride to obtain 8.2 g of a colorless liquid having a boiling point of 111° C. to 125° C. The colorless liquid had a strong sandalwood-like odor, and contained a mixture of 1-(8-ethyl-1,8-dimethyl-bicyclo[2,2,2]oct-5-ene-2-yl)-2-methyl-3-hydroxy-1-pentene and 1-(8-ethyl-5,8-dimethyl-bicyclo[2,2,2]oct-5-ene-3-yl)-2-methyl-3-hydroxy-1-pentene. The instrumental analytical results are shown below:

MS: M+ =262 m/e.
IR: 3325, 720 cm$^{-1}$.

SYNTHESIS EXAMPLE 4

Alloocimene (1) was isomerized by heating at 500° C., and the resulting mixture was used as a starting material without the separation of isomers. The mixture and acrolein were subjected to a Diels-Alder reaction to prepare a Diels-Alder adduct (a mixture of Compounds (6), (7), and (8) as described hereinbefore). Then, 22.1 g of the adduct was placed in a 200-ml reaction flask, and 70 ml of methanol, 46 ml of water, and 1 g of caustic soda were added thereto. While refluxing the mixture by heating, 7.4 g of propionaldehyde was dropwise added thereto over a period of one hour. After the dropwise addition was completed, the reaction was completed by heating for an additional three hours. The reaction solution was poured into ice water and extracted with ethyl ether. The ethyl ether layer was washed with water, dried using magnesium sulfate, and the ethyl ether was then distilled off. The residue was vacuum-distilled to obtain 10 g of a fraction having a boiling point of 100° to 106° C./1 mmHg. The instrumental analytical values of the fraction, i.e., the aldehyde compound are shown below:

MS: $M^+ = 232$ m/e.
IR: 2700, 1680, 1635 cm$^{-1}$.

Then, 20 ml of methanol, 0.5 g of a 10% aqueous solution of caustic potash, and 10 g of the aldehyde compound as prepared above were placed in a 100 ml reaction flask, and a solution consisting of 0.05 g of caustic potash, 10 ml of water, 10 ml of methanol, and 1 g of sodium boron hydride was dropwise added thereto at room temperature over a period of about one hour. The resulting mixture was stirred at room temperature for two hours and additionally at 55° C. for five hours to complete the reaction. The reaction solution was poured into 100 ml of ice water and extracted three times with 50 ml of ethyl ether. The ethyl ether layer was washed twice with 30 ml of a saturated saline solution, and dried with anhydrous Glauber's salt. Thereafter, the ethyl ether was distilled off. The residue was vacuum-distilled to obtain 9.4 g of a fraction having a boiling point of 100° C. to 110° C. at 1 mmHg. The fraction was a mixture of 1-(1,7,8,8-tetramethyl-bicyclo[2,2,2]oct-5-ene-2-yl)-2-methyl-3-hydroxy-1-propene, 1-(1,6,7,7-tetramethyl-bicyclo[2,2,2]oct-5-ene-2-yl)-2-methyl-3-hydroxy-1-propene, 1-(1,6,7,7-tetramethyl-bicyclo[2,2,2]oct-5-ene-3-yl)-2-methyl-3-hydroxy-1-propene, 1-(8-ethyl-1,8-dimethyl-bicyclo[2,2,2]oct-5-ene-2-yl)-2-methyl-3-hydroxy-1-propene, and 1-(8-ethyl-5,8-dimethyl-bicyclo[2,2,2]oct-5-ene-2-yl)-2-methyl-3-hydroxy-1-propene. The instrumental analytical values of the fraction are shown below:

MS: $M^+ = 234$ m/e.
IR: 3300 cm$^{-1}$.

The mixture had a camphor-like, musky, and sandalwood-like odor.

SYNTHESIS EXAMPLE 3

A 200-ml reaction flask was charged with 40 ml of a 4% aqueous solution of caustic potash which was then cooled to $-5°$ C. on an ice-salt bath, and 10 g of acetone was added thereto. Then, 19.2 g of the Diels-Alder adduct (a mixture of Compounds (6), (7), and (8) as used in Synthesis Example 4, which had been prepared from alloocimene, was dropwise added to the mixture over a period of 30 minutes. The resulting mixture was then reacted at $-5°$ C. for 4 hours and subsequently at room temperature for 72 hours. The reaction solution was poured into ice water and extracted with ethyl ether. The ethyl ether layer was washed with water, dried with magnesium sulfate, and concentrated. The residue was vacuum-distilled to obtain 12.5 g of a liquid having a boiling point of 100° C. to 110° C. at 1 mmHg. The instrumental analytical values of the liquid, i.e., ketone compound, were as follows:

MS: $M^+ = 232$ m/e.
IR: 1665, 1620 cm$^{-1}$.

Then, 12.5 g of the ketone compound was reduced with sodium boron hydride in the same manner as in Synthesis Example 4 to obtain 11.4 g of a liquid having a boiling point of 103° C. to 115° C. at 1 mmHg. The liquid was a mixture of 1-substituted-3-hydroxy-1-butenes containing a bicyclo[2,2,2]octene substituent, which were the same as those obtained in Synthesis Example 4. The liquid had a camphor-like, musky, and sandalwood-like odor. The instrumental analytical values of the liquid are as follows:

MS: $M^+ = 234$ m/e.
IR: 3320 cm$^{-1}$.

SYNTHESIS EXAMPLE 6

A 300-ml reaction flask was charged with 120 ml of methanol, 15 g of a 20% aqueous solution of caustic potash, and 40 g of methyl ethyl ketone. Then, 19.2 g of the same Diels-Alder adduct as used in Synthesis Example 4 (a mixture of Compounds (6), (7), and (8)) was added thereto at $-5°$ C. over a period of 30 minutes. The resulting mixture was reacted at $-5°$ C. for four hours and at room temperature for 72 hours. The reaction solution was then subjected to the same work-up as in Synthesis Example 4 to obtain 14.4 g of the corresponding ketone. The ketone compound was a liquid having a boiling point of 110° C. to 120° C. The instrumental analytical values of the ketone compound were as follows:

MS: $M^+ = 246$ m/e.
IR: 1660, 1620 cm$^{-1}$.

Then, 14.4 g of the ketone compound was reduced with sodium boron hydride in the same manner as in Synthesis Example 4 to obtain 12.9 g of a liquid having a boiling point of 115° C. to 120° C. at 1 mmHg. The liquid was a mixture of 1-substituted-2-methyl-3-hydroxy-1-butenes containing the bicyclo[2,2,2]octene substituent at the 1-position thereof, which were the same as those obtained in Synthesis Example 4. The liquid had a musky and sandalwood-like odor. The instrumental analytical values of the liquid are shown below:

MS: $M^+ = 234$ m/e.
IR: 3310 cm$^{-1}$.

SYNTHESIS EXAMPLE 7

A 1-liter reaction flask was charged with 328 g of methanol, 20 g of 40% caustic soda, and 164 g of diethyl ketone, which were then refluxed. A solution prepared by dissolving 82 g of the same Diels-Alder adduct as used in Synthesis Example 4 (a mixture of Compounds (6), (7), and (8)) in 82 g of methanol was dropwise added thereto over a period of one hour. The mixture was then refluxed for 20 hours, and the reaction solution was subjected to a post-treatment to obtain 60.5 g of a ketone compound. The ketone compound had a boiling point of 110° C. to 112° C. at 1 mmHg. The instrumental analytical values of the ketone compound were as follows:

MS: $M^+ = 260$ m/e.
IR: 1665, 1630 cm$^{-1}$.

Then, 100 ml of methanol, 2.5 g of a 10% aqueous solution of caustic potash, and 60.5 g of the ketone compound as prepared above were placed in a 500 ml reaction flask, and a solution consisting of 0.25 g of caustic potash, 50 ml of water, 50 ml of methanol, and 4 g of sodium boron hydride was added dropwise thereto at room temperature over a period of about one hour. The resulting mixture was reacted at room temperature for two hours and subsequently at 55° C. for five hours. The reaction solution was extracted with ethyl ether and subjected to work-up to thereby obtain 55 g of a liquid having a boiling point of 110° C. to 115° C./1 mmHg. The liquid was a mixture of 1-substituted-2-methyl-3-hydroxy-1-pentenes containing the bicyclo[2,2,2]octene substituent at the 1-position thereof, which were the same as those obtained in Synthesis Example 4, and it had a sandalwood-like odor. The instrumental analytical values of the liquid were as follows:

MS: M+ = 262 m/e.
IR: 3320 cm⁻¹.

SYNTHESIS EXAMPLE 8

A 300-ml autoclave was charged with 38.4 g of the same Diels-Alder adduct as was used in Synthesis Example 4 (a mixture of Compounds (6), (7), and (8)), 60 ml of ethanol, and 2 g of a 5% palladium-activated carbon catalyst. Hydrogenation was then performed under pressure of 20 kg/cm² at room temperature. After confirming that a theoretical amount of hydrogen was absorbed, the catalyst was filtered off. The filtrate was concentrated and vacuum-distilled to obtain 25.2 g of a mixture of bicyclo[2,2,2]octane carboxyaldehyde derivatives. The boiling point of the mixture thus-obtained was 66° C. to 69° C. at 1 mmHg. The instrumental analytical values are shown below:

MS: M+ = 194 m/e.
IR: 1720 cm⁻¹.

Then, 10 g of the mixture of bicyclo[2,2,2]octane carboxyaldehyde derivatives as prepared above, and 40 g of methyl ethyl ketone were reacted in methanol in the presence of a small amount of caustic soda in the same manner as in Synthesis Example 4 to prepare 6.5 g of a ketone compound. The boiling point of the ketone compound was 107° C. to 120° C. at 1 mmHg. The instrumental analytical values were as follows:

MS: M+ = 248 m/e.
IR: 1663, 1630 cm⁻¹.

Then, 6.5 g of the ketone compound was reduced with sodium boron hydride in the same manner as in Synthesis Example 4 and purified by distillation to obtain 6.0 g of a colorless liquid having a musky and sandalwood-like odor and a boiling point of 115° C. to 125° C. at 1 mmHg. The liquid thus-obtained was a mixture of 1-(1,7,8-tetramethyl-bicyclo[2,2,2]octane-2-yl)-2-methyl-3-hydroxyl-1-butene, 1-(1,6,7,7-tetramethyl-bicyclo[2,2,2]octane-2-yl)-2-methyl-3-hydroxy-1-butene, 1-(1,6,7,7-tetramethyl-bicyclo[2,2,2]octane-3-yl)-2-methyl-3-hydroxy-1-butene, 1-(8-ethyl-1,8-dimethyl-bicyclo[2,2,2]octane-2-yl)-2-methyl-3-hydroxy-1-butene, and 1-(8-ethyl-5,8-dimethyl-bicyclo[2,2,2]octane-2-yl)-2-methyl-3-hydroxy-1-butene. The instrumental analytical values were as follows:

MS: M+ = 250 m/e.
IR: 3310 cm⁻¹.

SYNTHESIS EXAMPLE 9

A ketone compound was prepared in the same manner as in Synthesis Example 8, except that 50 g of diethyl ketone was used in place of methyl ethyl ketone. The ketone substance was reduced to obtain 6.4 g of a colorless liquid having a boiling point of 115° C. to 125° C. at 1 mmHg. The colorless liquid was a mixture of 1-substituted-2-methyl-3-hydroxy-1-pentenes containing a bicyclo[2,2,2]octane substituent which were the same as those obtained in Synthesis Example 8. The colorless liquid has a camphor-like and sandalwood-like odor, and the instrumental analytical values thereof were as follows:

MS: M+ = 264 m/e.
IR: 3320 cm⁻¹.

EXAMPLE 1

A perfume base composition for a perfume or eau de Cologne was prepared by mixing the following ingredients:

|  | Parts by weight |
| --- | --- |
| Acetylcedrene | 100 |
| α-Hexylcinnamic aldehyde | 90 |
| Sandalwood oil | 70 |
| Rose base | 70 |
| Bergamot oil | 60 |
| Hydroxycitronellol | 60 |
| γ-Methylionone | 50 |
| Jasmine base | 50 |
| Phenylacetyl alcohol | 50 |
| Benzyl acetate | 40 |
| Ylang-ylang oil | 40 |
| Oakmoss absolute | 30 |
| Labdanum absolute | 20 |
| Isobutyl quinoline (10% triethyl citrate solution) | 20 |
| Undecanal (10% triethyl citrate solution) | 20 |
| Vanillin | 3 |
| Ethylvanillin | 2 |
| Compound obtained in Synthesis Example 1 | 220 |

A skilled perfumer has confirmed that the above prepared composition was a perfume base composition having a woody-type note, particularly a sandalwood-like aroma, which was well harmonized. Further, the composition was far excellent as compared to the same composition to which the compound obtained in Synthesis Example 1 was not added.

The same results as above were obtained when the compound obtained in Synthesis Example 7 was used in place of the compound obtained in Synthesis Example 1 in the above formulation.

EXAMPLE 2

A perfume base composition for eau de Cologne was prepared by mixing the following ingredients:

|  | Parts by weight |
| --- | --- |
| Coumarin | 300 |
| 4-Acetyl-6-tert-butyl-1,1-dimethylindan | 10 |
| Sandalwood oil | 200 |
| 4-(4-Hydroxy-4-methylpentyl)-tetrahydrobenzaldehyde | 30 |
| Amyl salicilate | 10 |
| Phenyl ethyl alcohol | 30 |
| α-Hexylcinnamic aldehyde | 30 |
| Benzyl acetate | 40 |
| γ-Methylionone | 10 |
| Civet tinc | 2 |
| Cedarwood oil | 200 |
| Eugenol | 5 |
| Citronellol | 15 |
| Hercolyn | 108 |
| Compound obtained in Synthesis Example 2 | 300 |

The thus-prepared composition was harmonized perfume in which a sandalwood-like characteristic note was emphasized, and was far excellent as compared to the same composition to which the compound obtained in Synthesis Example 2 was not added.

When the compound obtained in Synthesis Example 6 was used in place of the compound obtained in Synthesis Example 2 in the above formulation, similar results were obtained, although the perfume was changed to a more musky-like note.

EXAMPLE 3

A perfume base composition for eau de Cologne was prepared by mixing the following ingredients:

|   | Parts by weight |
|---|---|
| Patchouli oil | 150 |
| Vetiver oil | 40 |
| Geraniol | 40 |
| Citronellol | 40 |
| Geranium oil | 200 |
| Cyclopentadecanone | 50 |
| Coumarin | 50 |
| Eugenol | 30 |
| Cedar leaf oil | 20 |
| Cedarwood oil | 80 |
| Compound obtained in Synthesis Example 9 | 300 |

The panel consisting of five skilled perfumers checked their odor on paper broaders and confirmed that it was a perfume composition having camphor-like and sandalwood-like note in which the oriental tone was emphasized, and which was harmonized and provided a fresh feeling.

EXAMPLE 4

A perfume base composition for a toilet soap was prepared by mixing the following ingredients:

|   | Parts by weight |
|---|---|
| p-tert-Butylcyclohexyl acetate | 150 |
| Ethylene brassylate | 120 |
| Cedrol | 100 |
| Lavandine oil | 90 |
| Methylionone | 70 |
| Benzyl salicylate | 60 |
| α-Hexylcinnamic aldehyde | 50 |
| Benzyl acetate | 50 |
| Styrallyl salicylate | 40 |
| Isoamyl salicylate | 10 |
| Musk ketone | 30 |
| Dimethylbenzylcarvinyl acetate | 20 |
| Indole (10% triethylene citrate solution) | 20 |
| 9-Decenol-1 | 5 |
| Undecanal | 3 |
| Decanal | 2 |
| Compound obtained in Synthesis Example 8 | 150 |

When the above prepared perfume composition was applied in admixture of soap materials, there was obtained soap which had oriental type, musky, and sandalwood-like note with a fresh feeling.

EXAMPLE 5

|   | Parts by weight |
|---|---|
| Linallol | 50 |
| Cedarwood oil | 250 |
| Cedryl acetate | 150 |
| Coumarin | 20 |
| Guainac wood oil | 50 |
| α-Isomethylionone | 50 |
| Linalyl acetate | 30 |
| Patchouli oil | 50 |
| p-tert-Butylcyclohexyl acetate | 50 |
| Vetiver oil | 50 |
| Compound obtained in Synthesis Example 3 | 250 |

When the above prepared perfume composition was applied in admixture of soap materials, there was obtained soap which provided a fresh feeling in which a sandalwood-like note was emphasized with excellent tenacity.

EXAMPLE 6

A perfume base composition for synthetic detergent was prepared by mixing the following ingredients:

|   | Parts by weight |
|---|---|
| Cedarwood oil | 28 |
| Oakmoss | 54 |
| Coumarin | 40 |
| Musk ambrette | 42 |
| Acetylcedrene | 40 |
| Eugenol | 20 |
| Patchouli oil | 100 |
| Vetiver oil | 10 |
| Benzoin | 10 |
| Geranium oil | 20 |
| Lavandine oil | 10 |
| Citronellol | 30 |
| Geraniol | 40 |
| Citronella oil | 1 |
| Cinnamone oil | 2 |
| Ciste oil (10% triethyl citrate solution) | 3 |
| Methyldihydroabietate | 250 |
| Compound obtained in Synthesis Example 4 | 300 |

The thus prepared perfume composition enhanced the sandalwood-like note and had excellent retention. When it was used in synthetic detergent, the unpleasant odor of synthetic detergent materials was removed, and a fresh sandalwood-like perfume was obtained.

EXAMPLE 7

A perfume composition for a stick of incense was prepared by mixing the following ingredients:

|   | Parts by weight |
|---|---|
| Musk xylol | 20 |
| Vanillin | 8 |
| Civet tinc | 2 |
| Bromostyrene | 10 |
| Geranium oil | 30 |
| Patchouli oil | 30 |
| Cedarwood oil | 100 |
| Methyldihydroabietate | 300 |
| Compound obtained in Synthesis Example 7 | 500 |

The thus prepared perfume composition had strong sandalwood-like note. Thus, when it was used in admixture with incense materials, there was obtained a stick of incense which had excellent sandalwood-like aroma.

While the invention has been described in detail and with reference to specific embodiments thereof, it will be apparent to one skilled in the art that various changes and modifications can be made therein without departing from the spirit and scope thereof.

What is claimed is:

1. A perfume compound comprising at least one bicyclo[2,2,2]octane or bicyclo[2,2,2]octene derivative represented by formula (I)

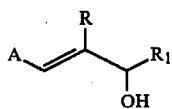

wherein R is a hydrogen atom or a methyl group, $R_1$ is a hydrogen atom, a methyl group, or an ethyl group, and A is

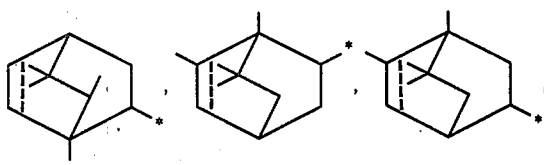

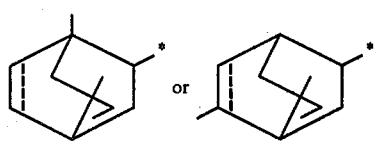

wherein the dotted line indicates the position of either a double bond or a single bond, and the asterisk* indicates the position of bonding to the remaining portion of formula (I).

2. The perfume compound of claim 1, wherein the bicyclo[2,2,2]octane or bicyclo[2,2,2]octene derivative has the structure:

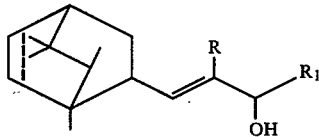

wherein R is a hydrogen atom or a methyl group, $R_1$ is a hydrogen atom, a methyl group, or an ethyl group, and the dotted line indicates the position of either a double bond or a single bond.

3. The perfume compound of claim 1, wherein the bicyclo[2,2,2]octane or bicyclo[2,2,2]octene derivative is a mixture of compounds having the structures:

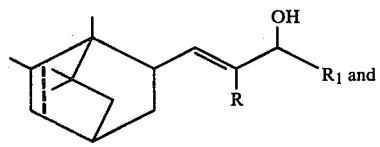

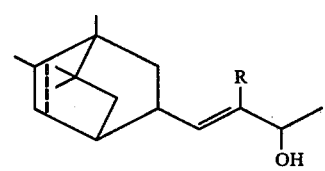

wherein R is a hydrogen atom or a methyl group, $R_1$ is a hydrogen atom, a methyl group or an ethyl group and the dotted line indicates the position of either a double bond or a single bond.

4. The perfume compound of claim 1, wherein the bicyclo[2,2,2]octane or bicyclo[2,2,2]octene derivative is a mixture of compounds having the structures:

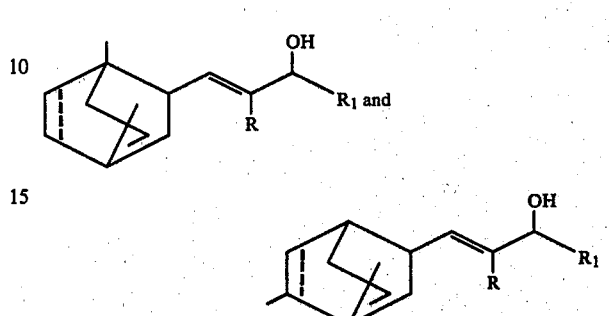

wherein R is a hydrogen atom or a methyl group, $R_1$ is a hydrogen atom, a methyl group or an ethyl group and the dotted line indicates the position of either a double bond or a single bond.

5. The perfume compound of claim 1, wherein the bicyclo[2,2,2]octane or bicyclo[2,2,2]octene derivative is a mixture of compounds having the structures:

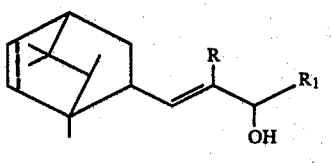

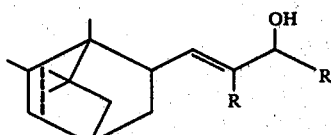

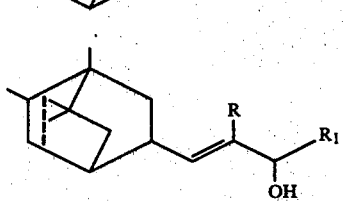

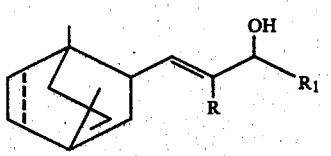

and

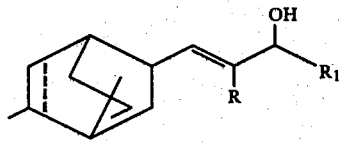

wherein R is a hydrogen atome or a methyl group, $R_1$ is a hydrogen atom, a methyl group or an ethyl group and the dotted line indicates the position of either a double bond or a single bond.

* * * * *